(12) United States Patent
Wang et al.

(10) Patent No.: US 11,794,992 B2
(45) Date of Patent: Oct. 24, 2023

(54) TRASH CONTAINER

(71) Applicants: Nine Stars Group (U.S.A.) Inc., Ontario, CA (US); Fujian Nashida Electronic Incorporated Company, Fuzhou (CN)

(72) Inventors: Xin Wang, Fuzhou (CN); Wennian Liu, Fuzhou (CN); Jiangqun Chen, Fuzhou (CN); Wenbin Ye, Fuzhou (CN); Youxi Luo, Fuzhou (CN); Shufeng Chen, Fuzhou (CN)

(73) Assignees: Nine Stars Group (U.S.A.) Inc., Ontario, CA (US); Fujian Nashada Electronic Incorporated Company, Fujian (CN)

( * ) Notice: Subject to any disclaimer, the term of this patent is extended or adjusted under 35 U.S.C. 154(b) by 0 days.

(21) Appl. No.: 17/971,900

(22) Filed: Oct. 24, 2022

(65) Prior Publication Data

US 2023/0046178 A1 Feb. 16, 2023

Related U.S. Application Data

(63) Continuation of application No. 16/716,457, filed on Dec. 16, 2019, now Pat. No. 11,505,402.

(51) Int. Cl.
 *B65F 1/16* (2006.01)
 *A61L 2/22* (2006.01)
 *A61L 2/24* (2006.01)

(52) U.S. Cl.
 CPC .............. *B65F 1/1638* (2013.01); *A61L 2/22* (2013.01); *A61L 2/24* (2013.01); *A61L 2202/23* (2013.01);
(Continued)

(58) Field of Classification Search
 CPC .............. B65F 1/1638; B65F 2210/129; B65F 2210/138; B65F 2210/168; A61L 2/22; A61L 2/24; A61L 2202/23
(Continued)

(56) References Cited

U.S. PATENT DOCUMENTS 4,660,758 A * 4/1987 Tavel .................... B65F 1/1436
312/211
7,516,865 B1 * 4/2009 Pierre ....................... B65F 7/00
220/908
(Continued)

FOREIGN PATENT DOCUMENTS

CN 107739221 A * 2/2018 ................ C05F 9/02
CN 109516023 A * 3/2019 ................ B65F 1/06
(Continued)

*Primary Examiner* — J. Gregory Pickett
*Assistant Examiner* — Niki M Eloshway
(74) *Attorney, Agent, or Firm* — Raymond Y. Chan; David and Raymond Patent Firm

(57) ABSTRACT

A trash container includes a container unit and an ultrasonic deodorizing device. The container unit includes a container having a top opening and a container cavity, and a container cover being moved between an opened position and a closed position. The ultrasonic deodorizing device includes a deodorizing carrier supported above the top opening of the container body for containing deodorant in liquid form, an ultrasonic nozzle operatively coupled at the deodorizing carrier for downwardly injecting the deodorant in an atomization manner below the top opening of the container body, and a nozzle controller configured to control and activate the ultrasonic nozzle.

20 Claims, 8 Drawing Sheets

(52) U.S. Cl.
CPC ... *B65F 2210/128* (2013.01); *B65F 2210/129* (2013.01); *B65F 2210/138* (2013.01); *B65F 2210/168* (2013.01)

(58) Field of Classification Search
USPC .......................................................... 220/87.1
See application file for complete search history.

(56) References Cited

U.S. PATENT DOCUMENTS

| | | | | |
|---|---|---|---|---|
| 8,771,606 | B2* | 7/2014 | Sun ........................... | A61L 2/10 206/362.1 |
| 10,022,467 | B2* | 7/2018 | Chang .................... | B65F 1/062 |
| 10,646,610 | B1* | 5/2020 | Tucker .................... | A61L 9/14 |
| 2002/0051739 | A1* | 5/2002 | Wang ........................ | A61L 2/202 422/116 |
| 2005/0028254 | A1* | 2/2005 | Whiting ................... | A61L 9/015 4/213 |
| 2008/0175751 | A1* | 7/2008 | Sun ........................... | A61L 9/20 422/5 |
| 2009/0261103 | A1* | 10/2009 | Watson .................... | B65F 7/00 220/495.07 |
| 2011/0056952 | A1* | 3/2011 | Borowski ............. | B65F 1/1484 383/127 |
| 2015/0122813 | A1* | 5/2015 | El-Taher ............... | B65F 1/1607 220/87.2 |
| 2016/0167873 | A1* | 6/2016 | Dunn ...................... | B65F 1/062 220/495.07 |
| 2017/0090447 | A1* | 3/2017 | Skocypec ................. | B65F 1/06 |
| 2018/0110893 | A1* | 4/2018 | Chang .................... | B65F 1/062 |
| 2018/0229932 | A1* | 8/2018 | DeGeorge ................. | B65F 1/16 |
| 2019/0112128 | A1* | 4/2019 | DeGeorge ........... | A01M 1/2044 |
| 2020/0087061 | A1* | 3/2020 | Cole ......................... | B65F 1/06 |
| 2020/0207544 | A1* | 7/2020 | Pestl ........................ | E05F 15/73 |
| 2021/0155405 | A1* | 5/2021 | Wei ......................... | B65F 1/068 |
| 2021/0283286 | A1* | 9/2021 | Dunn ........................ | A61L 2/24 |
| 2021/0290798 | A1* | 9/2021 | Johnson ................... | A61L 2/10 |
| 2022/0054695 | A1* | 2/2022 | Tucker .................. | A01K 1/0107 |

FOREIGN PATENT DOCUMENTS

| | | | | |
|---|---|---|---|---|
| CN | 110683253 A | * | 1/2020 | |
| KR | 2016114974 A | * | 10/2016 | ............. A61L 9/145 |
| KR | 2132951 B1 | * | 7/2020 | ............ B65F 1/1405 |
| KR | 2230985 B1 | * | 3/2021 | |
| TW | 201031579 A | * | 9/2010 | |
| WO | WO-2020010411 A1 | * | 1/2020 | ............ B65F 1/1421 |

* cited by examiner

TRASH CONTAINER

CROSS REFERENCE OF RELATED APPLICATION

This application is a Continuation application that claims the benefit of priority under 35 U.S.C. § 120 to a non-provisional application, application Ser. No. 16/716,457, filed Dec. 16, 2019, which is incorporated herewith by reference in its entirety.

BACKGROUND OF THE PRESENT INVENTION

Field of Invention

The present invention relates to a trash can, and more particularly to a trash container with an ultrasonic deodorizing device for eliminating waste odor in the trash container.

Description of Related Arts

An existing trash can, such as a household trash can, generally comprises a can body, a lid, and an actuation unit operatively moving the lid between an opened position and a closed position. For example, the actuation unit can be a foot actuator, wherein when the foot actuator is stepped or pressed by a foot of the user, the lid is moved from the closed position to the opened position. When the stepping force at the foot actuator is released, the lid is moved back to the closed position from the opened position. In another example, the actuation unit can be a touch sensor, wherein when the touch sensor is touched or contacted by a hand of the user, the lid is moved from the closed position to the opened position. Then, the lid is moved back to the closed position from the opened position after a predetermined time. Alternatively, the actuation unit can be a detection sensor, wherein when the detection sensor detects a presence of the user within a detection range of the detection sensor, the lid is moved from the closed position to the opened position, wherein the lid is moved back to the closed position from the opened position after a predetermined time.

A common problem with the trash can, especially the kitchen trash can, is the elimination of waste material and odors emanating from the waste materials. In fact, the indoor trash can and outdoor trash cannot eliminate the waste material, cannot stop emanating odors from the waste materials, and cannot sterilize the waste material. As a result, the existing trash can cannot stop the air pollution and bacterial growth, so as to affect people health.

One method to remove the odors from the waste material is the use of trash bag made of deodorizing material, such that the trash bag is able to partially absorb the odors from the waste materials. However, the cost of the trash bag will be increased and the deodorizing power of the trash bag is ineffective and limited depending on the waste type and amount of the waste materials.

Another method is the use of deodorizing agent applied in the trash can via an applicator. Accordingly, the operation of the lid and the operation of the deodorizing applicator are separated that the user must operate the lid and the deodorizing applicator individually. The structure of the trash can will be complicated when incorporating with the deodorizing applicator, so as to highly increase the manufacturing cost of the trash can with the deodorizing applicator. In addition, the deodorizing applicator is inconvenient to use and the deodorizing power is limited. In other words, the trash can with the deodorizing applicator is impracticable in use, such that the deodorizing applicator is not customized for using in the indoor trash can, such as residential trash can or office trash can, or in the outdoor trash can such as commercial or industrial trash can.

SUMMARY OF THE PRESENT INVENTION

The invention is advantageous in that it provides a trash container, which comprises an ultrasonic deodorizing device for eliminating waste odor in the trash container.

Another advantage of the invention is to provide a trash container, wherein the deodorant is downwardly injected in an atomization manner below a top opening of the container body via an ultrasonic nozzle for eliminating waste odor in the container body.

Another advantage of the invention is to provide a trash container, wherein the ultrasonic nozzle is controlled to be actuated for inject the deodorant at different conditions. For example, the ultrasonic nozzle is actuated after the container cover is moved back to the closed position from the opened position. In addition, the ultrasonic nozzle is actuated when the container cover is retained at the closed position after a predetermined idling time.

Another advantage of the invention is to provide a trash container, wherein the ultrasonic nozzle is controlled in response to an automatic actuation of the container cover, so as to simplify the operation of the ultrasonic deodorizing device incorporating with the operation of the container cover.

Another advantage of the invention is to provide a trash container, wherein the deodorizing carrier is supported above the container body to prevent any pollution from the trash in the container body and to maximize the usage volume of the container cavity.

Another advantage of the invention is to provide a trash container, wherein the trash information of the trash container can be collected and analyzed for classifying the trash and quantity of the trash in the trash container.

Another object of the present invention is to provide a trash container, which does not require to alter the original structural design of the trash container, so as to minimize the manufacturing cost of the trash container incorporating with the ultrasonic deodorizing device.

Another object of the present invention is to provide a trash container, wherein no expensive or complicated structure is required to employ in the present invention in order to achieve the above mentioned objects. Therefore, the present invention successfully provides an economic and efficient solution for providing a sterilized, odor free, and clean configuration for the trash container to prevent any contamination of the induction container by the trash.

Additional advantages and features of the invention will become apparent from the description which follows, and may be realized by means of the instrumentalities and combinations particular point out in the appended claims.

According to the present invention, the foregoing and other objects and advantages are attained by a trash container, comprising:

a container unit which comprises a container body having a top opening and a container cavity for collecting trash therein, and a container cover movably coupled at the container body between an opened position and a closed position; and an ultrasonic deodorizing device which comprises:

a deodorizing carrier supported above the top opening of the container body for containing deodorant in liquid form;

an ultrasonic nozzle operatively coupled at the deodorizing carrier for downwardly injecting the deodorant in an atomization manner below the top opening of the container body; and a nozzle controller configured to control and activate the ultrasonic nozzle.

In accordance with another aspect of the invention, the present invention comprises a trash managing method of a trash container, comprising the following steps.

(A) Move a container cover from a closed position to an opened position to open up a top opening of a container body for disposing trash into a container cavity of the container body.

(B) Activate an ultrasonic nozzle of an ultrasonic deodorizing device by a nozzle control to actuate the ultrasonic nozzle for downwardly injecting a deodorant in an atomization manner below the top opening of the container body into the container cavity.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
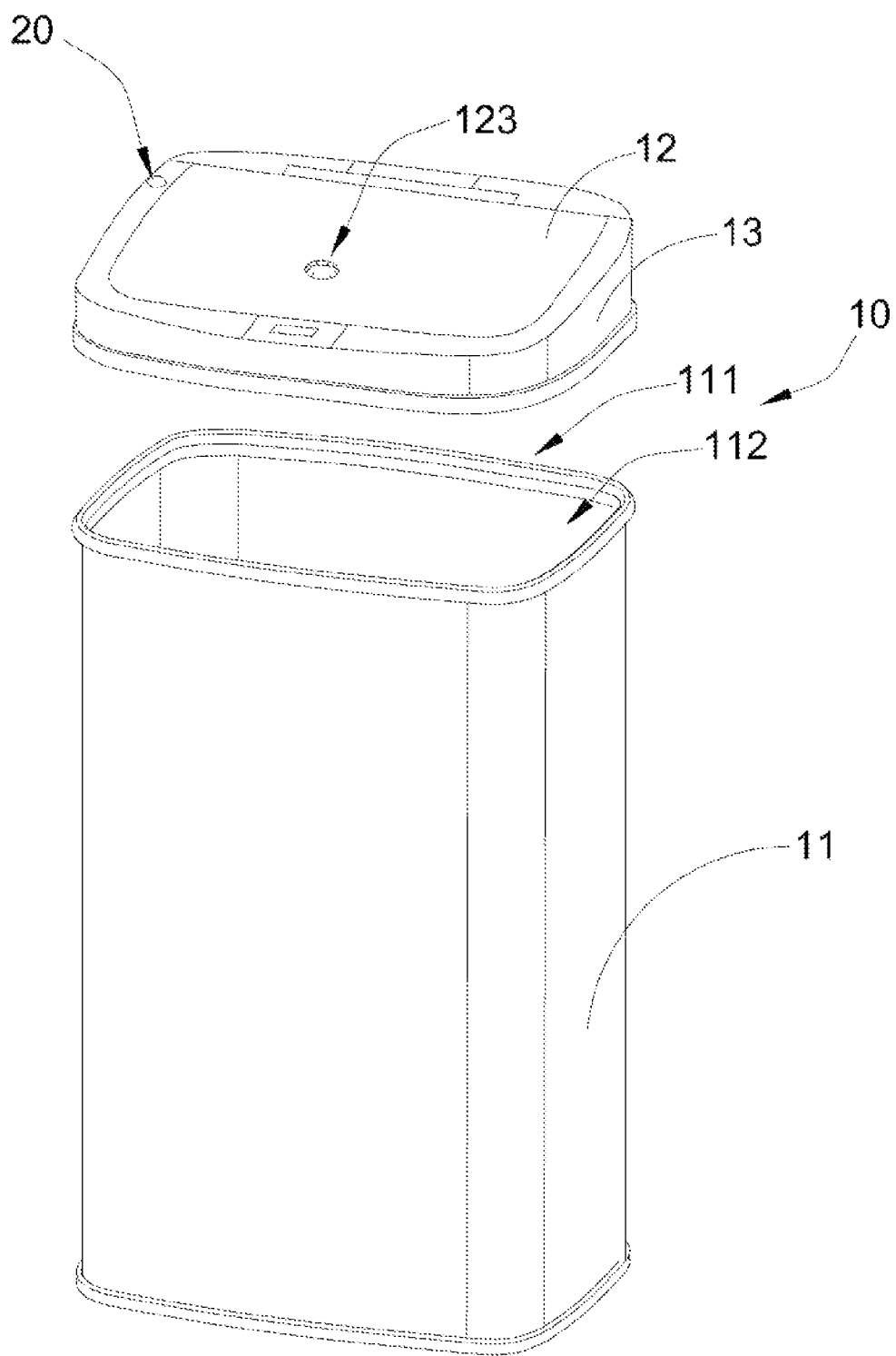
FIG. 1 is a perspective view of a trash container according to a preferred embodiment of the present invention.
Figure 2:
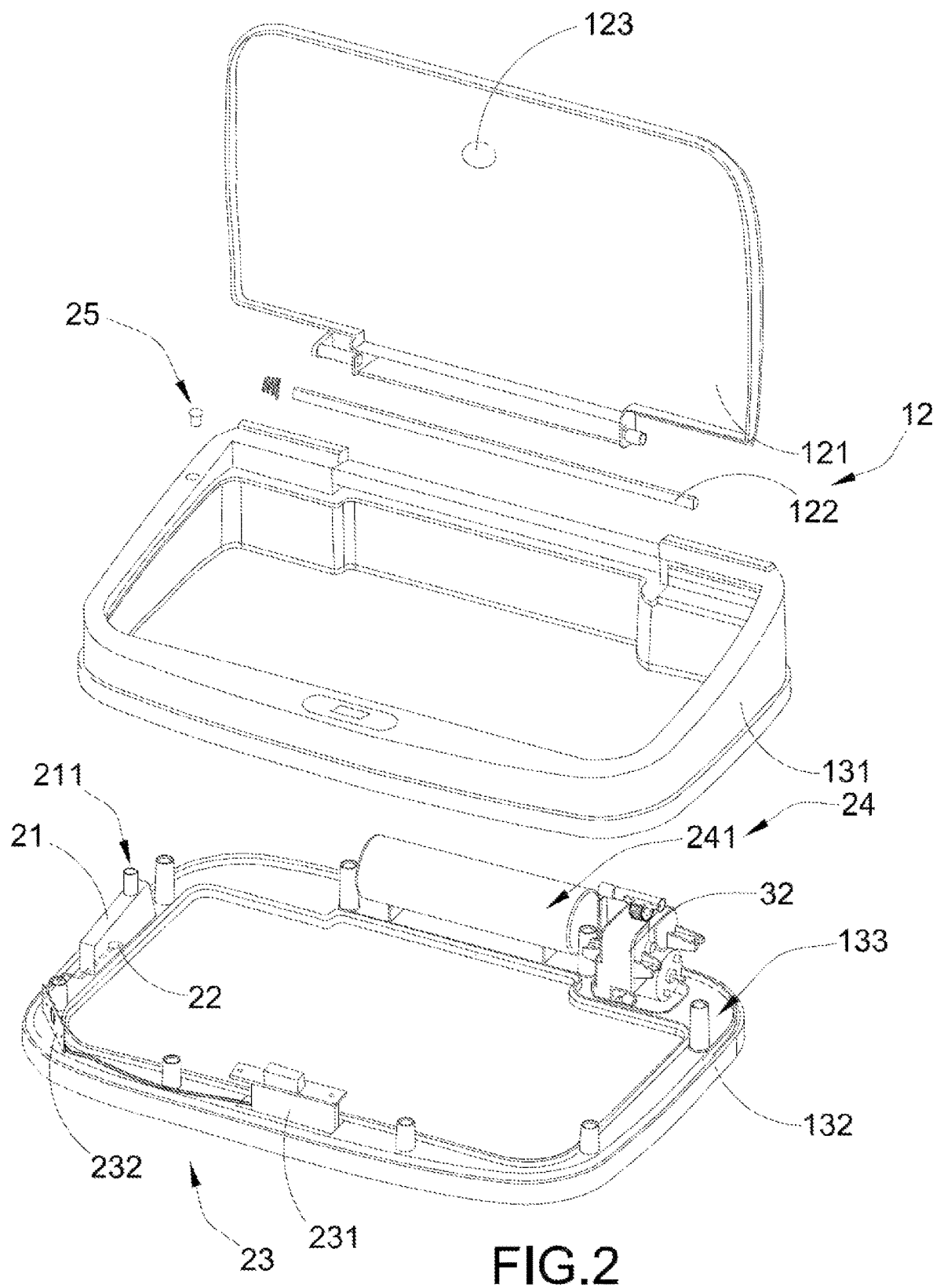
FIG. 2 is an exploded perspective view of a control housing of the trash container according to the above preferred embodiment of the present invention, illustrating the trash container incorporating with an ultrasonic deodorizing device.
Figure 3:
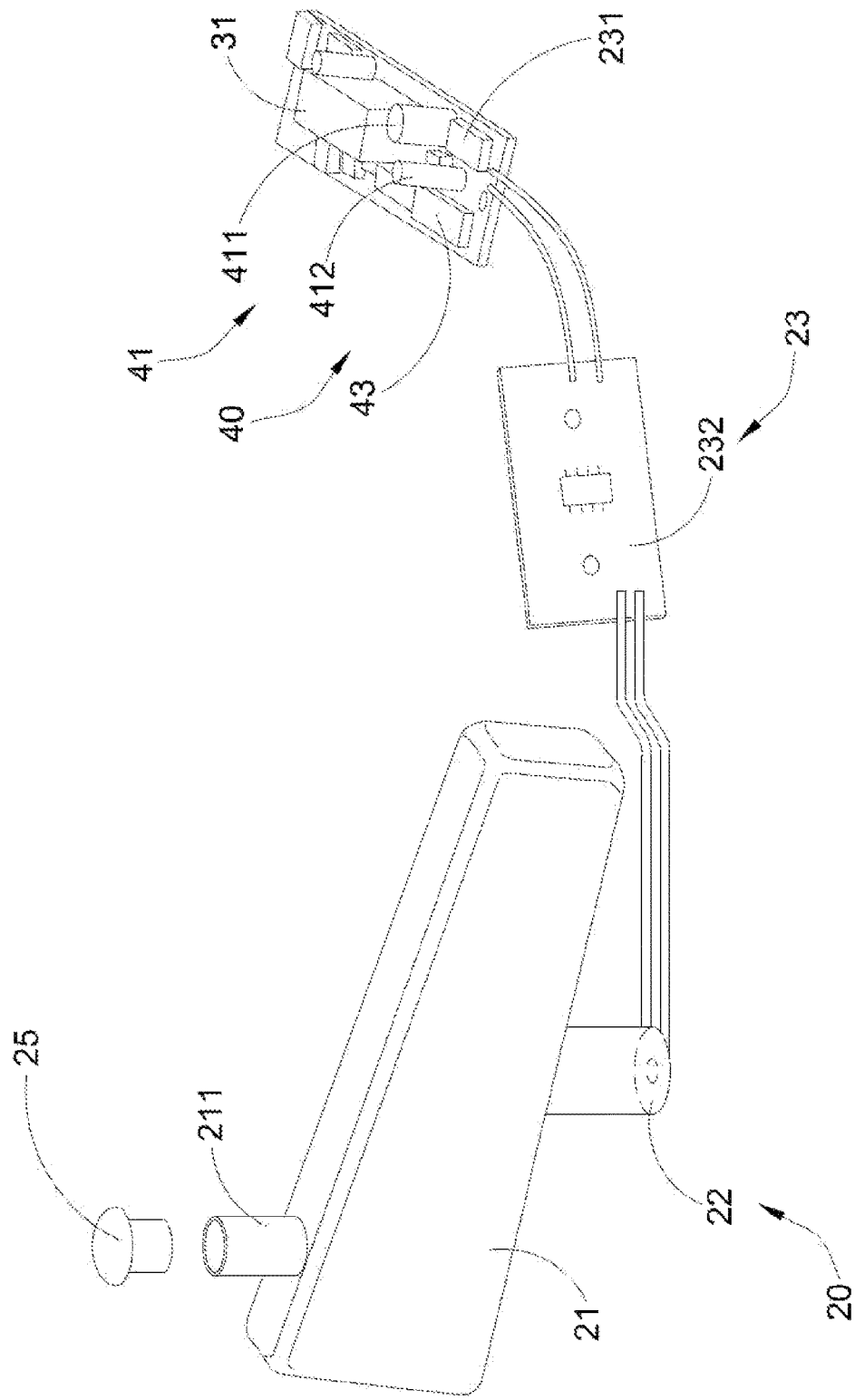
FIG. 3 is a perspective view of the ultrasonic deodorizing device of the trash container according to the above preferred embodiment of the present invention.
Figure 4:
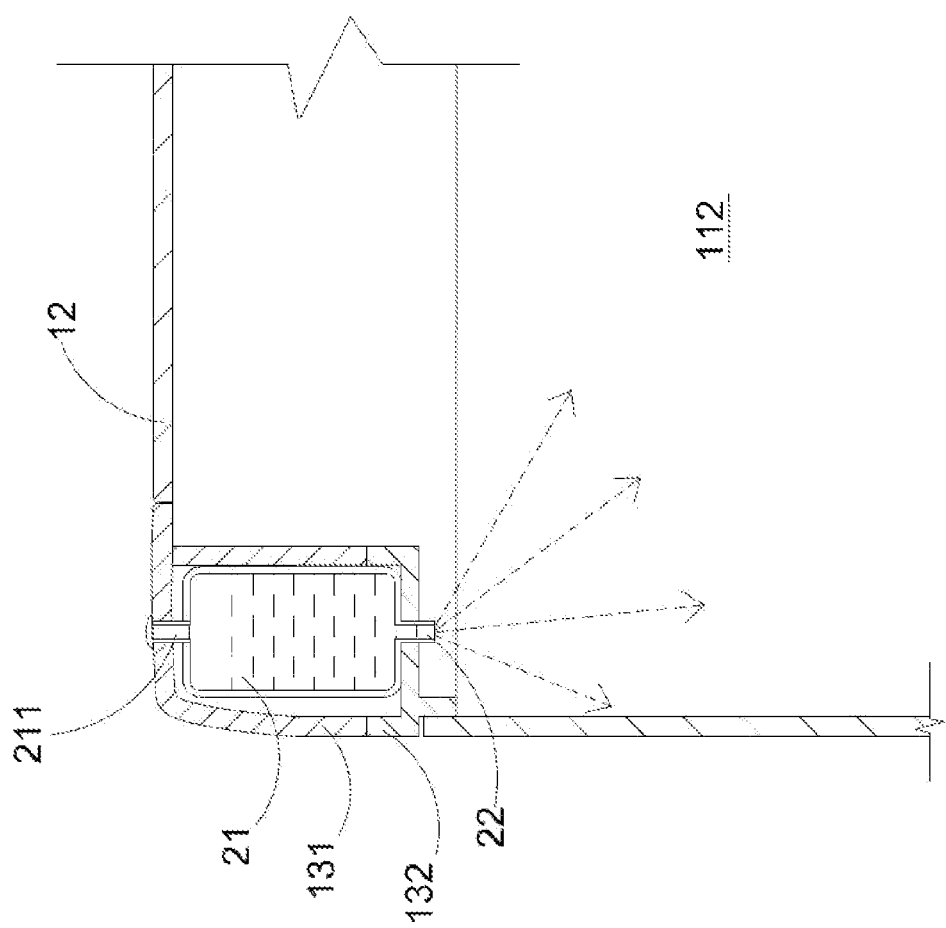
FIG. 4 is a partially sectional view of the trash container according to the above preferred embodiment of the present invention, illustrating the operation of the ultrasonic deodorizing device.
Figure 5:
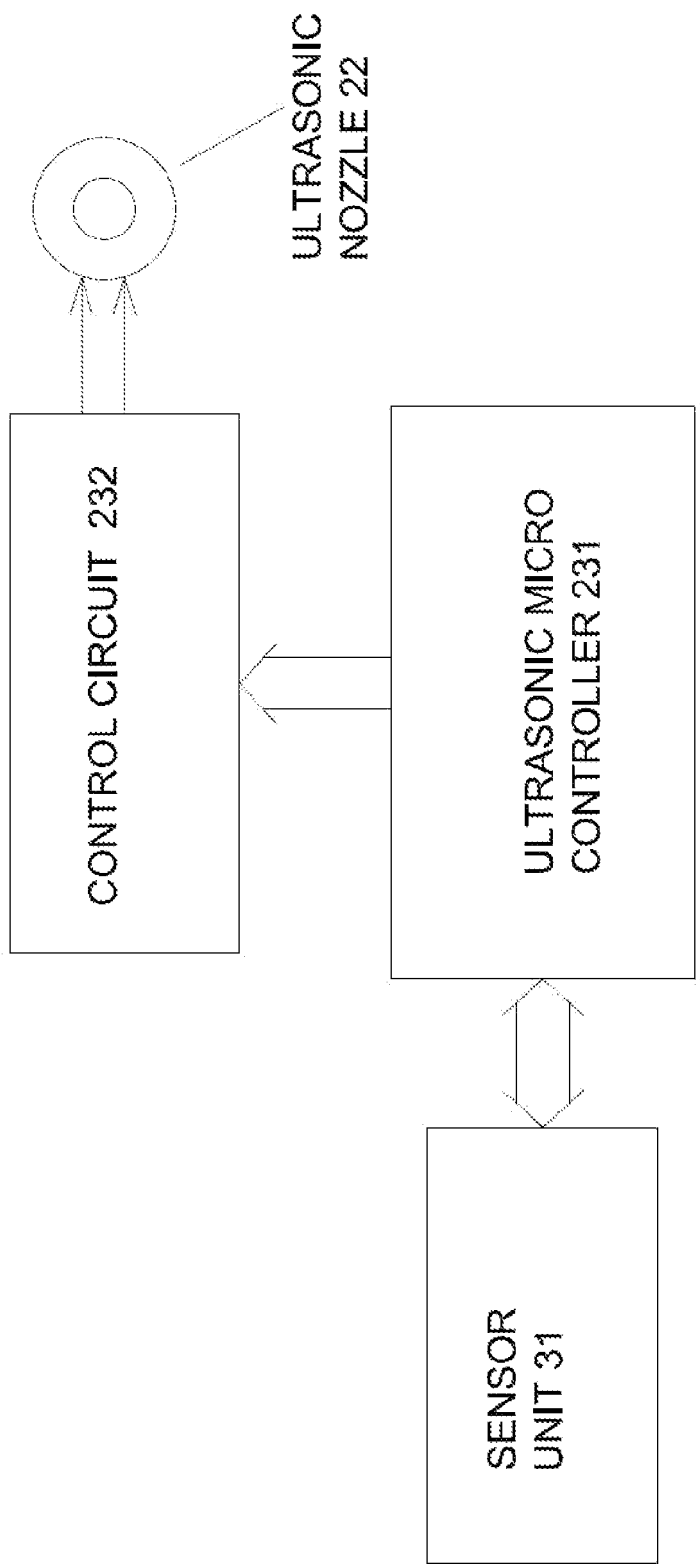
FIG. 5 is a block diagram illustrating the ultrasonic deodorizing device of the trash container according to the above preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIGS. 1 to 4 of the drawings, a trash container according to a preferred embodiment of the present invention is illustrated, wherein the trash container comprises a container unit 10 and a deodorizing device 20.

The container unit 10, such as a household trash container, comprises a container body 11 and a container cover 12. The container body 11 has a top opening 111 and a container cavity 112 for collecting trash therein. The container cover 12 is movably coupled at the container body 11 and is actuated to move between an opened position and a closed position. At the opened position, the container cover 12 is moved to expose the top opening 111 of the container body 11 for disposing the trash into the container cavity 112. At the closed position, the container cover 12 is moved to cover the top opening 111 of the container body 11 for enclosing the container cavity 112.

The container unit 10 further comprises a control housing 13 for supporting the container cover 12 above the top opening 111 of the container body 11. Accordingly, the control housing 13 has a bottom side detachably supported on the top opening 111 of the container 11, and a top side, wherein the container cover 12 is pivotally coupled at the top side of the control housing 13.

Particularly, the control housing 13 comprises an upper housing frame 131 and a lower housing frame 132 detachably coupled at the container body 11 around the top opening 111 thereof. The container cover 12 is pivotally coupled at the upper housing frame 131. Accordingly, the upper housing frame 131 has a cover opening communicating with the top opening 111, wherein the container cover 12 is pivotally coupled at the upper housing frame 131 at the cover opening thereof. The lower housing 132, having an annular structure, is detachably coupled at a top edge of the container body 11 around the top opening 111 thereof. Furthermore, the upper housing frame 131 is coupled on the lower housing frame 132 to define a concealed compartment 133 within the upper and lower housing frames 131, 132. It is worth mentioning that the concealed compartment 133 can be partitioned into a front compartment portion, a rear compartment portion, and two side compartment portions. Accordingly, the container cover 12 comprises a cover panel 121 pivotally coupled at the upper housing frame 131 via a cover shaft 122.

According to the preferred embodiment, the deodorizing device 20 comprises a deodorizing carrier 21 supported above the top opening 111 of the container body 11 for containing deodorant in liquid form, a nozzle 22 operatively coupled at the deodorizing carrier 21 for downwardly injecting the deodorant into the container cavity 112, and a nozzle controller 23 configured to control and activate the ultrasonic nozzle 22. Preferably, the deodorizing device 20 is an ultrasonic deodorizing device 20, wherein the nozzle 22 is an ultrasonic nozzle 22 operatively coupled at the deodorizing carrier 21 for downwardly injecting the deodorant in an atomization manner below the top opening 111 of the container body 11.

As shown in FIGS. 2 to 5, the deodorizing carrier 21, preferably made of plastic, is received in the control housing 13 in order to elevate the deodorizing carrier 21 above the top opening 111 of the container body 11 below the container cover 12. Particularly, the deodorizing carrier 21 is received at one of the side compartment portions of the concealed compartment 133 of the control housing 13. In other words, the deodorizing carrier 21 is supported on the lower housing frame 132 and is received at one side of the upper housing frame 131. Therefore, the size of the deodorizing carrier 21 can be maximized by the size of the control housing 13 to contain the deodorant. For example, the control housing 13 has a trapezoid shape to have a flat bottom side and a slanted top side, wherein the deodorizing carrier 21 has the corresponding trapezoid shape to have a flat bottom side and a slanted top side.

It is worth mentioning that the deodorant is able to remove waste odor from the trash in the trash container. The deodorant can also have sterilizing ability for minimizing the bacterial growth in the trash container. The deodorant can a deodorizing and sterilizing liquid composed of microorganisms (probiotics). The microorganisms of the probiotics are harmless to the human body, and are easy to survive and reproduce in a high-humidity organic environment, such that the deodorant can deodorize the kitchen waste and provide excellent sterilization effect.

A deodorant inlet 211 of the deodorizing carrier 21 is extended to the top side of the control housing 13 for filling the deodorant, wherein the ultrasonic nozzle 22 is extended through the bottom side of said control housing 13, such that the ultrasonic nozzle 22 is actuated to inject or spray the deodorant into the container cavity 112. Accordingly, the deodorant inlet 211 of the deodorizing carrier 21 is formed at the upper housing frame 131 of the control housing 13 while the ultrasonic nozzle 22 is extended through the lower housing frame 132 of the control housing 13. In other words, an inlet opening is formed at the top side of the upper housing frame 131, wherein the deodorant inlet 211 of deodorizing carrier 21 is extended to the inlet opening of the upper housing frame 131. An nozzle opening is formed at the bottom side of the lower housing frame 132, wherein the ultrasonic nozzle 22 is coupled at the bottom side of the deodorizing carrier 21 to the nozzle opening of the lower housing frame 132. An inlet stopper 25 is detachably coupled at the deodorant inlet 211 of the deodorizing carrier 21 to close the deodorizing carrier 21. The inlet stopper 25 can be detached from the deodorant inlet 211 in order to refill the deodorant in the deodorizing carrier 21.

The ultrasonic nozzle 22 is arranged for injecting the deodorant in an atomization manner, such that the deodorant is transformed into a plurality of micro droplets to increase the surface tension of the deodorant, such that the deodorant can be evenly adhered on the trash in the trash container. It is worth mentioning that since the deodorizing carrier 21 is received at one side of the control housing 13, the ultrasonic nozzle 22 is actuated for injecting the deodorant at an angle toward a center of the container cavity 112. Alternatively, the ultrasonic nozzle 22 can be supported at a slanted configuration for injecting the deodorant at an angle toward the center of the container cavity 112.

According to the preferred embodiment, the nozzle controller 23 is configured to control and activate the ultrasonic nozzle 22 in order to actuate the ultrasonic nozzle 22 for completing the injecting operation thereof. The nozzle controller 23 comprises an ultrasonic micro controller 231 and a control circuit 232 operatively linked to the ultrasonic nozzle 22 and configured to actuate the ultrasonic nozzle 22 for injecting the deodorant in response to a movement of the container cover 12. In one embodiment, the control circuit 232 comprises an ultrasonic activation circuit electrically linked to the ultrasonic micro controller 231, such that when the ultrasonic micro controller 231 is activated, the ultrasonic nozzle 22 is actuated via the control circuit 232 for injecting the deodorant.

Accordingly, the control circuit 232 is delayed to actuate the ultrasonic nozzle 22 after the container cover 12 is moved back to the closed position from the opened position. In other words, when the container cover 12 is moved to close the top opening 111 of the container body 11, the ultrasonic nozzle 22 is automatically actuated for spraying the deodorant into the container cavity 112 of the container body 11 so as to keep the deodorant therein. Preferably, when the container cover 12 is moved at the opened position, the control circuit 232 will activate the ultrasonic nozzle 22, such as activate the ultrasonic nozzle 22 from a sleep mode to a standby mode. Therefore, once the container cover 12 is moved to close the top opening 111 of the container body 11, the ultrasonic nozzle 22 is automatically actuated for spraying the deodorant into the container cavity 112 of the container body 11.

Furthermore, the control circuit 232 is programmed in such a manner that the control circuit 232 is configured to actuate the ultrasonic nozzle 22 when the container cover 12 is retained at the closed position after a predetermined idling time, such as every 2 to 5 hours, so as to prevent the bacteria growth and odor acclimated in the container unit 10. In other words, the ultrasonic nozzle 22 is actuated frequently when the container cover 12 is closed. In one example, the ultrasonic nozzle 22 is actuated every 3 hours when the container cover 12 is closed.

It is worth mentioning that the injection volume of the deodorant can be controlled at each injection operation of the ultrasonic nozzle 22 and at different conditions. For example, the ultrasonic nozzle 22 is configured to inject 0.2 ml to 0.6 ml, preferably 0.3 ml, of deodorant every time when the container cover 12 is moved to the closed position. The ultrasonic nozzle 22 is configured to inject 0.3 ml to 0.9 ml, preferably 0.5 ml, of deodorant every time when the container cover 12 is stayed at the closed position after a predetermined idling time. The injection volumes of the deodorant are set differently at different conditions. Since the container cover 12 is frequently moved between the opened and closed positions during the peak hours, such as preparing dinner, the injection amount of deodorant can be reduced. During the idling time of the container cover 12, such as the nighttime, the injection amount of deodorant may be increased to maintain the deodorant in the container cavity 112 for the next injection time. In other words, the injection volume of the deodorant in response to the opened-and-closed movement of the container cover 12 is less than the injection volume of the deodorant in response to the container cover 12 in an idling manner.

According to the preferred embodiment, the trash container further comprises an actuation module 30 for automatically actuating the container cover between the opened position and the closed position. In one embodiment, the actuation unit 30 comprises a sensor unit 31 operatively linked to the control circuit 232 through the ultrasonic micro controller 231, and a motorized unit 32 operatively controlled by the control circuit 232, such that when the sensor unit 31 is activated, the control circuit 232 is configure to actuate the motorized unit 32 to move the container cover 12 from the closed position to the opened position and is configured to actuate the ultrasonic nozzle 22 for injecting the deodorant.

Accordingly, the sensor unit 31 is a detection sensor having a predetermined detecting range, wherein the sensor unit 31 is received in the front compartment portion of the concealed compartment 133 of the control housing 13 for detecting a movement in front of the container unit 10 through a sensor window of the upper housing frame 131.

For example, when the sensor unit 31 detects the user's movement in front of the container unit 10, the sensor unit 31 will send a sensor signal to the control circuit 232, such that the control circuit 232 will send a first actuating signal to the motorized unit 32 for actuating the container cover 12 to move from the normal closed position to the opened position. After a predetermined opening time, the control circuit 232 will send a second actuating signal to the motorized unit 32 for actuating the container cover 12 to move back to its normal closed position from the opened position. It is worth mentioning that when the control circuit 232 sends the second actuating signal to the motorized unit 32, the control circuit 232 will also sends a nozzle actuating signal to the ultrasonic nozzle 22, such that ultrasonic nozzle 22 will be actuated for injecting the deodorant once the container cover 12 is closed.

It is appreciated that the sensor unit 31 can be a touch sensor defining a touch area on the upper housing frame 131, such that when the sensor unit 31 is touched or contacted, such as by a user's hand, the sensor unit 31 will send a sensor signal to the control circuit 232. The container cover 12 will be actuated to move between the opened and closed positions.

Likewise, the container cover 12 further has a manual handle 123 provided on a top side of the cover panel 121, wherein the container cover 12 is adapted to be manually actuated between the opened and closed positions by the manual handle 123. In other words, the user is able to pivotally open the container cover 12 by lifting up the manual handle 123 and to pivotally close the container cover 12 by dropping down the manual handle 123. Correspondingly, the sensor unit 31 can be a position sensor for detecting the position of the container cover 12.

The motorized unit 32 is received in the rear compartment portion of the concealed compartment 133 of the control housing 13. Accordingly, the motorized unit 32 has a gear assembly operatively coupled at the cover shaft 122 to pivotally move the cover panel 121. Preferably, the motorized unit 32 is adapted to generate reversible rotating powers to the cover shaft 122, such that when the first rotating power is generated by the motorized unit 32 to the cover shaft 122, the cover panel 121 is moved from the closed position to the opened position. When the opposed second rotating power is generated by the motorized unit 32 to the cover shaft 122, the cover panel 121 is moved to the closed position from the opened position. The reversible rotating powers are generated by the motorized unit 32 in response to the first and second actuating signals from the control circuit 232.

According to the preferred embodiment, the ultrasonic deodorizing device 20 further comprises a power source 24 electrically linked to the control circuit 232 and the actuation module 30 to form a common power supply. The power source 24 comprises a battery compartment 241 formed at the rear compartment portion of the concealed compartment 133 of the control housing 13, wherein one or more batteries, such as rechargeable batteries or disposable batteries, can be received in the battery compartment 241 to supply electrical power to the control circuit 232 and the actuation module 30. In other words, the control circuit 232, the sensor unit 31, and the motorized unit 32 are powered by the same power source 24.

Figure 7:
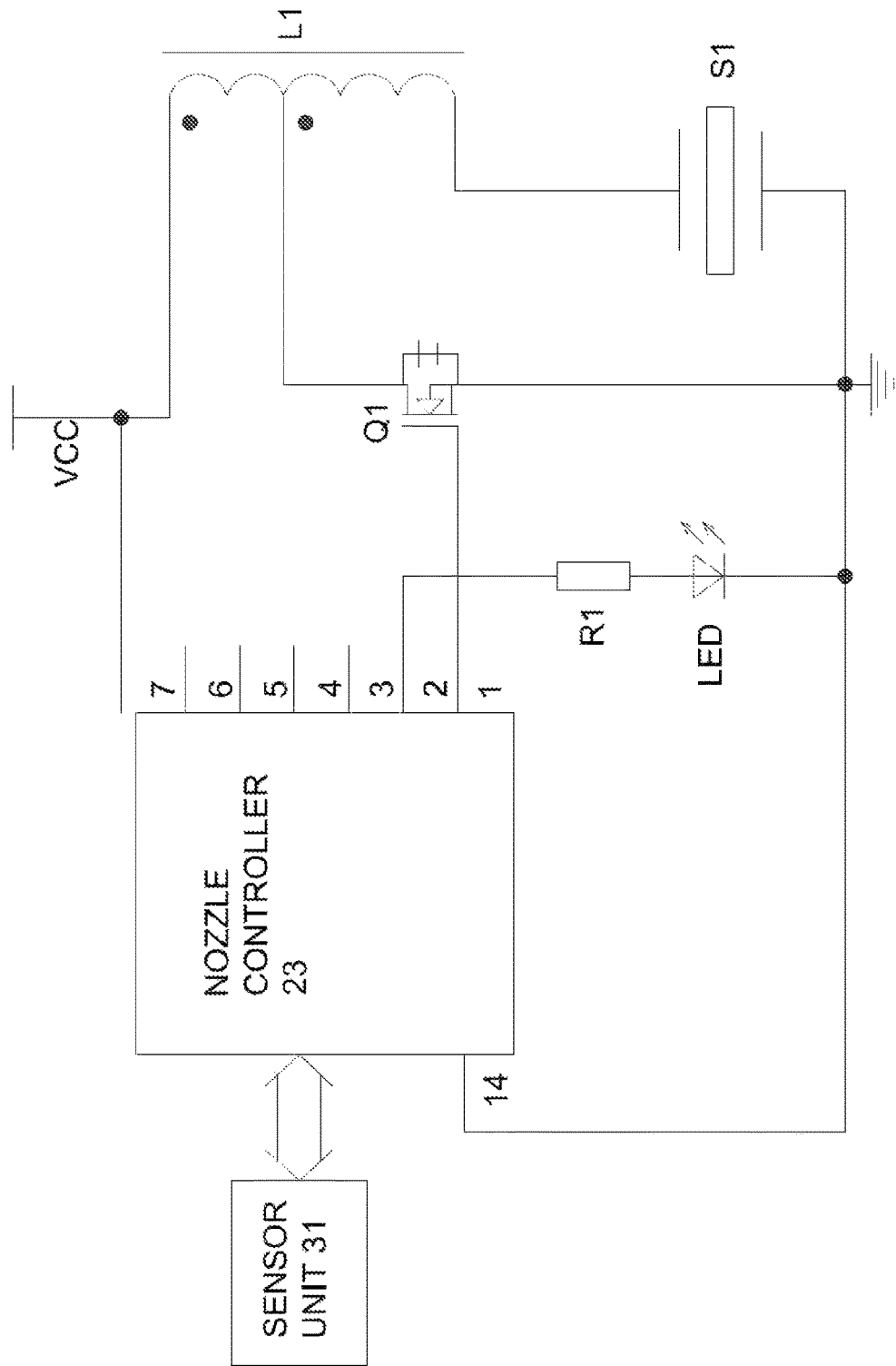
FIG. 7 is a circuit diagram illustrating the ultrasonic deodorizing device of the trash container according to the above preferred embodiment of the present invention.

FIG. 7 is a circuit diagram illustrating the ultrasonic deodorizing device 20 incorporated with the actuation module 30, wherein the nozzle controller 23 is electrically connected to the sensor unit 31. The circuit is configured as follows: The nozzle controller 23 has a plurality of terminals, such as from first terminal to seventh terminal, and a fourteen terminal. The first terminal of the nozzle controller 23 is electrically connected to a gate of a field effect transistor Q1. The seventh terminal of the nozzle controller 23 is electrically connected to VCC, wherein VCC is electrically connected to an inductor L1. The inductor L1 is electrically connected to a drain of the transistor Q1, wherein the transistor Q1 is electrically grounded. The second terminal of the nozzle controller 23 is electrically connected to a resistor R1 and one end of a LED respectively, wherein another end of the LED is electrically grounded. The fourteen terminal of the nozzle controller 23 is electrically grounded. An ultrasonic atomizing element S1 is electrically connected between the inductor L1 and a ground connecting wire. When initiating the injection operation, the first terminal of the nozzle controller 23 is configured to output a signal, such as 105 kHz, to the gate of the transistor Q1, wherein the transistor Q1 and the inductor L1 form a feedback loop. Through the voltage boost of the inductor L1 (about 50V), the ultrasonic atomizing element S1 is actuated and vibrated to inject the deodorant in an atomization manner.

According to the preferred embodiment, the trash container further comprises a monitoring module 40 for monitoring the condition of the trash container. Accordingly, the monitoring module 40 comprises a data collector 41 coupled at the container unit 10 for collecting trash information thereof and/or user data, and a fluid monitor 42 operatively coupled to the ultrasonic deodorizing device 20 for monitoring the deodorant in the deodorizing carrier 21.

Figure 8:
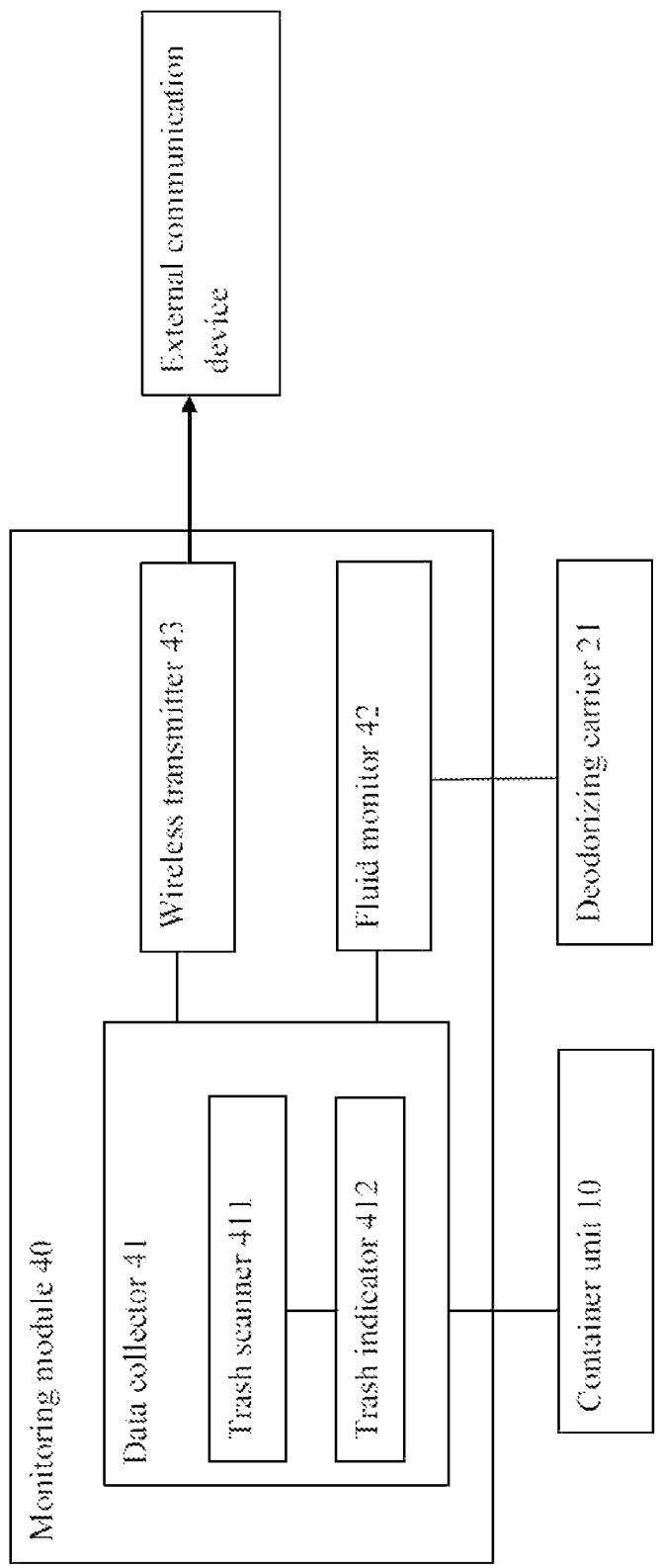
FIG. 8 is a block diagram illustrating a data collector of the trash container according to the above preferred embodiment of the present invention.

As shown in FIG. 8, the data collector 41 comprises a trash scanner 411 coupled at the container unit 10 for classifying the trash and quantity of the trash therein as the trash information, and a trash indicator 412 indicating the trash information. In one embodiment, the trash scanner 411 can be a camera device supported at the front compartment portion of the concealed compartment 133 of the control housing 13 for capturing images of the trash being disposed in the container cavity 112. The image signal will be sent to the trash indicator 412 for further processing and analyzing. For example, the trash indicator 412 will indicate the trash as a recyclable trash or non-recyclable trash. The trash indicator 412 will further indicate the amount of the trash in the container cavity 112 to notify the user when the container cavity 112 is full. In one example of setting the container unit 10 a recycle bin, the trash indicator 412 will indicate the user the improper trash in the container unit 10 when the non-recyclable trash is thrown in the container cavity 112.

The fluid monitor 42 is operatively linked to the trash indicator 412 and is configured for indicating a fluid level of the deodorant in the deodorizing carrier 21. When the fluid monitor 42 detects the fluid level of the deodorant in the deodorizing carrier 21 below a certain level, the trash indicator 412 will notify the user to refill the deodorant in the deodorizing carrier 21.

The monitoring module 40 further comprises a wireless transmitter 43 operatively linked to the data collector 41 for wirelessly transmitting the trash information to an external communicative device. For example, the monitoring module 40 can be wirelessly connected to the user's smartphone via the wireless transmitter 43, such that the user is able to view all the trash information and the fluid level of the deodorant by the smartphone.

It is appreciated that the trash container can be the residential, commercial, community, or industrial trash container sharing with more than one families/workers or a public trash container, wherein the waste odor in the trash container can be removed by the deodorizing device 20 to prevent any air pollution. In addition, the monitoring module 40 will monitor the trash information to classify the type of trash and to prevent any prohibited trash, such as electronic waste, being thrown in the trash container without any permission. Furthermore, the monitoring module 40 can wirelessly linked to a city health department or other management office, which can immediately send an operator/officer to pick up or clean the trash when the trash container is full so as to prevent the overfill of the trash that causes the land pollution.

Figure 6:
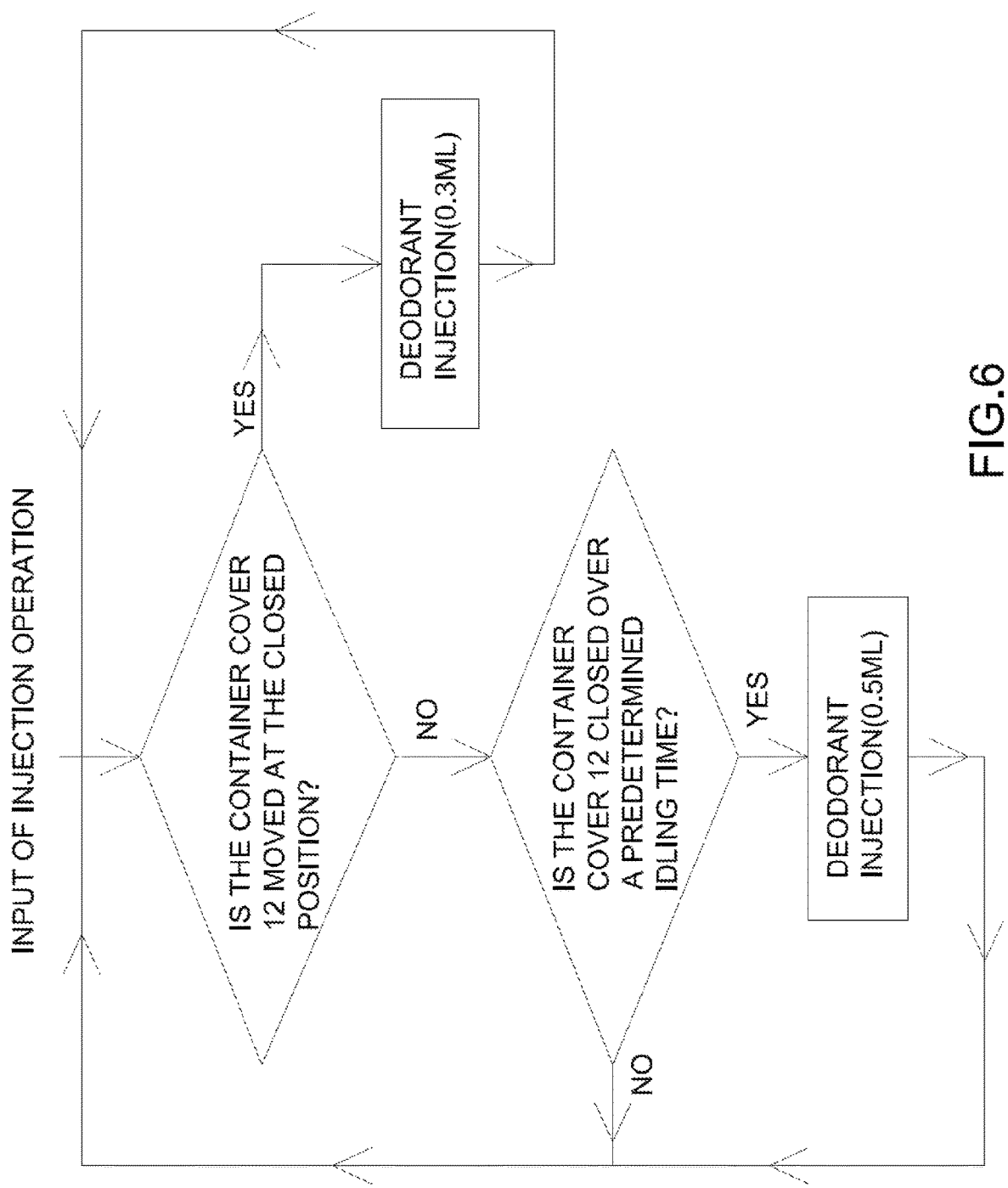
FIG. 6 is a flow diagram illustrating the operation of the trash container according to the above preferred embodiment of the present invention.

As shown in FIG. 6, the present invention further provides a trash managing method of the trash container, comprising the following steps.

(1) Move the container cover 12 from the closed position to the opened position to open up the top opening 111 of the container body 11 for disposing the trash into the container cavity 112 of the container body 11.

(2) Activate the ultrasonic nozzle 22 by the nozzle control 232 to actuate the ultrasonic nozzle 22 for downwardly injecting the deodorant in an atomization manner below the top opening 111 of the container body 11 into the container cavity 112.

(3) Collect trash information of the trash container via the data collector 41.

(4) Monitor the deodorant in said deodorizing carrier 21 via the fluid monitor 42.

According to the preferred embodiment, the step (1) further comprises the following steps.

(1.1) Detect a presence of a user via the sensor unit 31, wherein the sensor unit 31 can be a motion sensor for detecting the user movement in front of the container unit 10 or a touch sensor for being activated by a touch or contact of the user.

(1.2) Automatically actuate the container cover 12 via the motorized unit 32 to move from the closed position to the opened position. Accordingly, the control circuit 232 will send the first actuating signal to the motorized unit 32 for actuating the container cover 12 to move from the normal closed position to the opened position and subsequently the control circuit 232 will send the second actuating signal to the motorized unit 32 for actuating the container cover 12 to move back to its normal closed position from the opened position. At the same time, when the second actuating signal is generated, the control circuit 232 will sends the nozzle actuating signal to the ultrasonic nozzle 22.

In the step (2), the ultrasonic nozzle 22 is actuated when the container cover 12 is moved back to the closed position from the opened position. In addition, the ultrasonic nozzle 22 is configured to actuate when the container cover 12 is retained at the closed position after a predetermined idling time. It is worth mentioning that the ultrasonic nozzle 22 is activated when the container cover 12 is moved from the closed position to the opened position, and is actuated for injection operation when the container cover 12 is moved back to the closed position from the opened position.

According to the preferred embodiment, the step (3) further comprises the following steps.

(3.1) Classify the trash and quantity of the trash therein as the trash information via the trash scanner 411.

(3.2) Indicate the trash information via the trash indicator 412. It is worth mentioning that the fluid level of the deodorant in the deodorizing carrier is also indicated by the trash indicator 412.

(3.3) Wirelessly transmit the trash information to an external communicative device via the wireless transmitter 43.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A trash managing method of a trash container, comprising steps of:
   (a) moving a container cover from a closed position to an opened position to open up a top opening of a container body of a container unit for disposing trash into a container cavity of said container body; and
   (b) activating an ultrasonic nozzle of an ultrasonic deodorizing device, which comprises a deodorizing carrier received in a concealed compartment formed in a control housing coupled on said container body for supporting said container cover above said top opening of said container body and supporting said deodorizing carrier above said top opening of said container body to operatively couple said ultrasonic nozzle, by a nozzle controller to actuate said ultrasonic nozzle for injecting a deodorant, in an atomization manner, from said deodorizing carrier at an angle toward said container cavity.

2. The trash managing method, as recited in claim 1, wherein, in the step (b), said ultrasonic nozzle is actuated when said container cover is moved back to said closed position from said opened position.

3. The trash managing method, as recited in claim 1, wherein, in the step (b), said ultrasonic nozzle is actuated when said container cover is retained at said closed position after a predetermined idling time.

4. The trash managing method, as recited in claim 1, wherein the step (b) further comprises steps of:
   (b.1) filling the deodorant in the deodorizing carrier through an inlet thereof; and
   (b.2) activating said ultrasonic nozzle when said container cover is moved from said closed position to said opened position.

5. The trash managing method, as recited in claim 1, wherein the step (a) further comprises steps of:
   (a.1) detecting a presence of a user via a sensor unit; and
   (a.2) automatically actuating said container cover via a motorized unit to move from said closed position to said opened position.

6. The trash managing method, as recited in claim 5, wherein said motorized unit and said nozzle control are electrically powered by a common power source.

7. The trash managing method, as recited in claim 5, further comprising steps of:
   (c) collecting trash information of said trash container via a data collector; and
   (d) monitoring the deodorant in said deodorizing carrier via a fluid monitor.

8. The trash managing method, as recited in claim 7, wherein the step (c) further comprises steps of:
   (c.1) classifying the trash and quantity of the trash therein as said trash information via a trash scanner;
   (c.2) indicating said trash information via a trash indicator; and (c.3) wirelessly transmitting the trash information to an external communicative device via a wireless transmitter.

9. The trash managing method, as recited in claim 1, further comprising steps of:
(c) collecting trash information of said trash container via a data collector; and
(d) monitoring the deodorant in said deodorizing carrier via a fluid monitor.

10. The trash managing method, as recited in claim 9, wherein the step (c) further comprises steps of:
(c.1) classifying the trash and quantity of the trash therein as said trash information via a trash scanner;
(c.2) indicating said trash information via a trash indicator; and
(c.3) wirelessly transmitting the trash information to an external communicative device via a wireless transmitter.

11. A trash container, comprising:
a container unit which comprises a container body having a top opening and a container cavity for collecting trash therein, a control housing having a top side, a bottom side and a concealed compartment formed between said top side and said bottom side, and a container cover movably coupled at said container body between an opened position and a closed position, wherein said bottom side of said control housing is detachably supported on said top opening of said container body and said container cover is pivotally coupled at said top side of said control housing; and
an ultrasonic deodorizing device which comprises:
a deodorizing carrier, received in said concealed compartment of said control housing, being supported above said top opening of said container body for containing a deodorant in liquid form, wherein said deodorizing carrier has a deodorant inlet for filling the deodorant in said deodorizing carrier;
an ultrasonic nozzle operatively coupled at said deodorizing carrier for downwardly injecting the deodorant in an atomization manner below said top opening of said container body, wherein said ultrasonic nozzle is extended through said bottom side of said control housing for injecting the deodorant at an angle toward said container cavity; and
a nozzle controller configured to control and activate said ultrasonic nozzle to infect the deodorant, in an atomization manner, into said container cavity.

12. The trash container, as recited in claim 11, wherein said nozzle controller comprises a control circuit operatively linked to said ultrasonic nozzle and configured to actuate said ultrasonic nozzle for injecting the deodorant in response to a movement of said container cover.

13. The trash container, as recited in claim 12, wherein said control circuit is delayed to actuate said ultrasonic nozzle after said container cover is moved back to said closed position from said opened position.

14. The trash container, as recited in claim 13, further comprising an actuation module configured to automatically actuate said container cover between said opened position and said closed position, wherein said actuation unit comprises a sensor unit operatively linked to said control circuit and a motorized unit operatively controlled by said control circuit, such that when said sensor unit is activated, said control circuit is configure to actuate said motorized unit to move said container cover from said closed position to said opened position and is configured to actuate said ultrasonic nozzle for injecting the deodorant.

15. The trash container, as recited in claim 14, wherein said control circuit is configured to actuate said ultrasonic nozzle when said container cover is retained at said closed position after a predetermined idling time.

16. The trash container, as recited in claim 14, wherein said ultrasonic deodorizing device further comprises a power source electrically linked to said control circuit and said actuation module to form a common power supply.

17. The trash container, as recited in claim 12, further comprising an actuation module configured to automatically actuate said container cover between said opened position and said closed position, wherein said actuation unit comprises a sensor unit operatively linked to said control circuit and a motorized unit operatively controlled by said control circuit, such that when said sensor unit is activated, said control circuit is configure to actuate said motorized unit to move said container cover from said closed position to said opened position and is configured to actuate said ultrasonic nozzle for injecting the deodorant.

18. The trash container, as recited in claim 12, wherein said control circuit is configured to actuate said ultrasonic nozzle when said container cover is retained at said closed position after a predetermined idling time.

19. A trash container, comprising:
a container unit which comprises a container body having a top opening and a container cavity for collecting trash therein, a control housing having a concealed compartment, and a container cover movably coupled at said container body between an opened position and a closed position, wherein said control housing has a bottom side detachably supported on said top opening of said container body and a top side pivotally couple with said container cover, wherein said concealed compartment is formed between said top side and said bottom side, such that said deodorizing carrier has a deodorant inlet extended to said top side of said control housing for filling the deodorant while said ultrasonic nozzle is extended through said bottom side of said control housing; and
an ultrasonic deodorizing device which comprises:
a deodorizing carrier, received in said concealed compartment of said control housing, being supported above said top opening of said container body for containing deodorant in liquid form;
an ultrasonic nozzle operatively coupled at said deodorizing carrier for downwardly injecting the deodorant in an atomization manner below said top opening of said container body; and
a nozzle controller configured to control and activate said ultrasonic nozzle.

20. The trash container, as recited in claim 19, wherein said deodorizing carrier comprises a carrier body defining a deodorizing compartment for receiving the deodorant therein and an inlet channel upwardly extended from a top side of said carrier body to define said deodorant inlet, wherein said ultrasonic nozzle is coupled at said bottom side of said carrier body, wherein said deodorizing carrier is received at one side of said control housing that said ultrasonic nozzle is actuated for injecting the deodorant at an angle toward a center of said container cavity.

* * * * *